(12) United States Patent
Biswas et al.

(10) Patent No.: US 10,252,986 B2
(45) Date of Patent: Apr. 9, 2019

(54) PROCESS FOR THE PREPARATION OF EXAMETAZIME

(71) Applicant: Jubilant Life Sciences Limited, Uttar Pradesh (IN)

(72) Inventors: Sujay Biswas, Uttar Pradesh (IN); Vikas Bansal, Uttar Pradesh (IN); Rohit Chakravarty, Uttar Pradesh (IN); Mokkapati Umamaheshwar Prasad, Uttar Pradesh (IN); Mukesh Masand, Uttar Pradesh (IN); Dharam Vir, Uttar Pradesh (IN)

(73) Assignee: JUBILANT GENERICS LIMITED, Uttar Pradesh (IN)

( * ) Notice: Subject to any disclaimer, the term of this patent is extended or adjusted under 35 U.S.C. 154(b) by 96 days.

(21) Appl. No.: 15/124,003

(22) PCT Filed: Mar. 17, 2015

(86) PCT No.: PCT/IB2015/051928
§ 371 (c)(1),
(2) Date: Sep. 6, 2016

(87) PCT Pub. No.: WO2015/145302
PCT Pub. Date: Oct. 1, 2015

(65) Prior Publication Data
US 2017/0015620 A1   Jan. 19, 2017

(30) Foreign Application Priority Data
Mar. 27, 2014 (IN) .............................. 883/DEL/2014

(51) Int. Cl.
| | |
|---|---|
| *C07C 249/12* | (2006.01) |
| *C07B 57/00* | (2006.01) |
| *C07C 249/14* | (2006.01) |
| *C07C 249/04* | (2006.01) |

(52) U.S. Cl.
CPC ............ *C07C 249/12* (2013.01); *C07B 57/00* (2013.01); *C07C 249/04* (2013.01); *C07C 249/14* (2013.01); *C07B 2200/07* (2013.01)

(58) Field of Classification Search
None
See application file for complete search history.

(56) References Cited

U.S. PATENT DOCUMENTS 4,789,736 A   12/1988   Canning et al.

FOREIGN PATENT DOCUMENTS

| CS | 276287 B6 | 1/1992 |
|---|---|---|
| EP | 0 194 843 A2 | 9/1986 |
| KR | 0134565 B1 | 12/1997 |
| KR | 0615893 B1 | 8/2006 |
| KR | 0632963 B1 | 9/2006 |

OTHER PUBLICATIONS

Ding, H-J et al. 2000 "An efficient one-pot method for the large-quantitative production of radiopharmaceutical ligand: Diazadioximes" *Chem Pharm Bull* 48(2): 288-289.

Vanderghinste, et al. 2003 "An efficient HPLC method for the analysis of isomeric purity of technetium-99-exametazime and identity confirmation using LC-MS" *J. Pharm. Biomed. Anal.* 32: 679-685.

*Primary Examiner* — Sudhakar Katakam
*Assistant Examiner* — Jennifer C Sawyer
(74) *Attorney, Agent, or Firm* — Knobbe, Martens, Olson & Bear, LLP

(57) ABSTRACT

The present invention provides an improved process for the preparation of exametazime, which is used as ligand in preparation of technetium-99m complex.

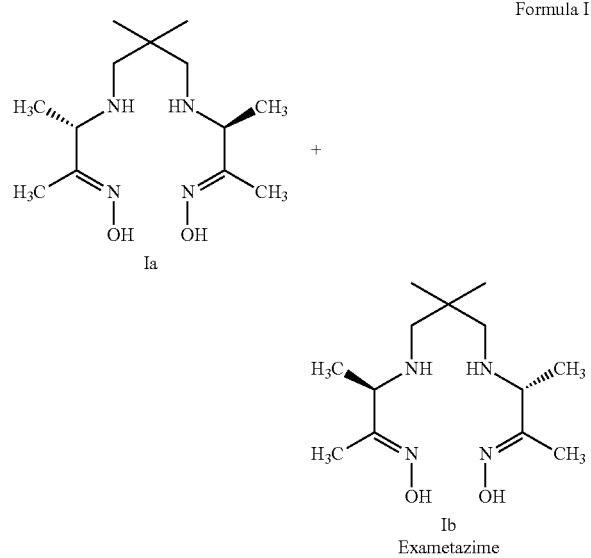

6 Claims, No Drawings

PROCESS FOR THE PREPARATION OF EXAMETAZIME

FIELD OF THE INVENTION

Present invention relates to improved process for the preparation of exametazime, which is used as ligand in preparation of technetium-99m complex.

BACKGROUND OF THE INVENTION

Exametazime (formula I) is a propylene amine oxime ligand, which is used for the preparation of lipophilic technetium-99m (Tc-99m) complex. This complex is used as diagnostic aid (radioactive imaging agent) as an adjunct in the detection of altered regional cerebral perfusion in stroke and localization of intra-abdominal infection and inflammatory bowel disease.

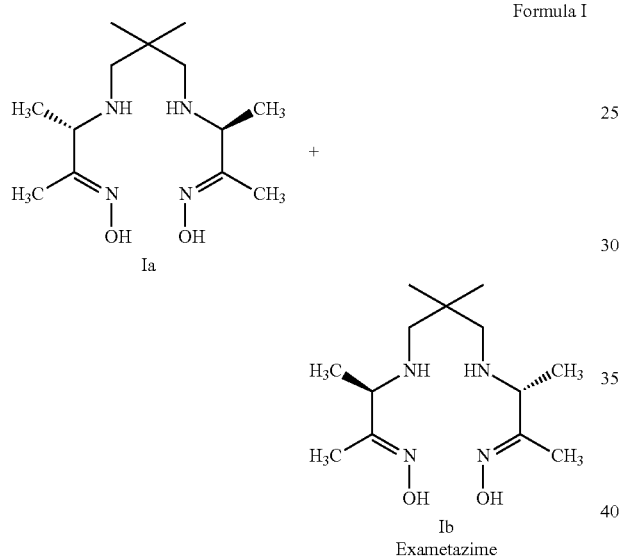

Formula I

The complex is marketed by GE Healthcare under brand name Ceretec® kit, which is having strength of 0.5 mg exametazime per vial as injectable.

Exametazime is chemically known as (SS,RR)-4,8-diaza-3,6,6,9-tetramethyl undecane-2,10-dione bisoxime, formerly it was also known as hexamethylpropylene amine oxime (HMPAO). Exametazime is a racemic mixture of d' (formula Ia) and 'l' (formula Ib) enantiomers. Exametazime and its lipophilic complex with technetium-99m (Tc-99m) are specifically covered in expired U.S. Pat. No. 4,789,736, assigned to Amersham International PLC.

U.S. Pat. No. 4,789,736 discloses preparation of exametazime (Scheme 1), which involves reaction of 2,3-butanedione monoxime (formula II) with 2,2-dimethyl-1,3-propanediamine (formula III) in benzene, in presence of acetic acid to afford diimine derivative 4,8-diaza-3,6,6,9-tetramethylundecane-3,8-diene-2,10-dione bisoxime (formula IV). Benzene is known to be carcinogenic and is not used as solvent, as per the current norms. The diimine derivative is reduced with sodium borohydride in aqueous ethanol followed by double recrystallization from acetonitrile to afford pure product, which is a mixture of 'd', 'l' and meso isomers. U.S. Pat. No. 4,789,736 further discloses methods for separation of meso and d, l-isomers either by normal-phase HPLC or by fractional crystallisation. Fractional crystallization method involves double recrystallization of crude product from acetonitrile to afford dl-enriched material, which is further subjected to slow recrystallization from ethyl acetate to afford enantiomerically pure dl isomer i.e. exametazime, as large clear crystals.

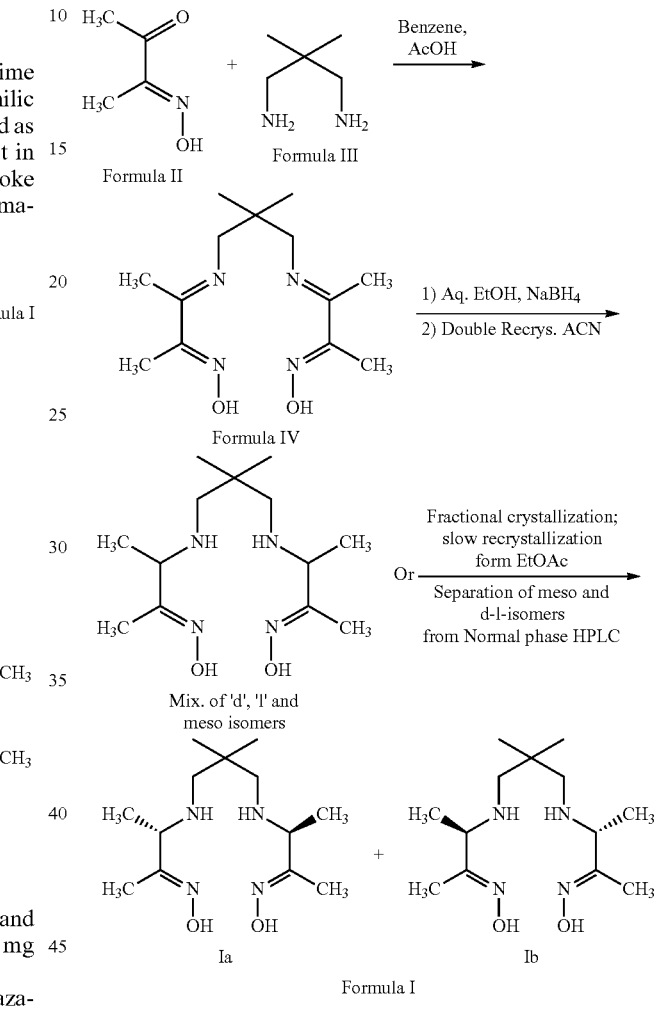

U.S. Pat. No. 4,789,736 reported 0.8~0.9% of exametazime (formula I) yield from a mixture of 'l' and meso isomers via fractional recrystallization.

CS276287B6 assigned to Ustav Jaderneho Vyzkumu, discloses preparation of exametazime (Scheme 2), the process involves reaction of 2,3-butanedione monoxime (formula II) with 2,2-dimethyl-1,3-propanediamine (formula III) in benzene, in presence of weak acid cation Amberlite IRC-50 catalyst to afford diimine derivative 4,8-diaza-3,6,6,9-tetramethylundecane-3,8-diene-2,10-dione bisoxime (formula IV). Benzene is known to be carcinogenic and is not used as solvent, as per the current norms. The diimine derivative is reduced with sodium borohydride in aqueous ethanol to afford crystals of 'd', 'l' and meso isomers. These crystals are recrystallized three times with ethyl acetate to give undesired pure meso form. The filtrate of reduction step is diluted with water and extracted with chloroform. The extracts are evaporated and further recrystallized five times from ethyl acetate to afford exametazime.

The said process involves multiple recrystallizations, which in turn reduces the overall yield of exametazime.

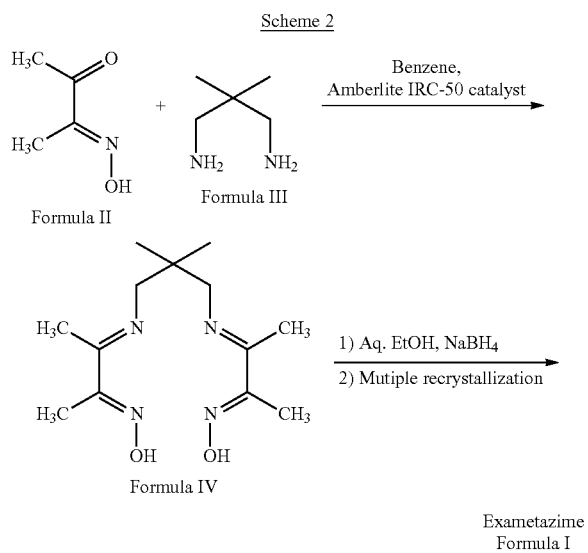

Scheme 2

KR134565B1 assigned to Korea Inst. Sci. & Tech., discloses reductive amination method which involves reaction of 2,3-butanedione monoxime (formula II) with 2,2-dimethyl-1,3-propanediamine (formula III) in anhydrous methanol, in presence of sodium cyano borohydride to afford a mixture of 'd', 'l' and meso isomers. This mixture is recrystallized in ethyl acetate to afford exametazime (Scheme 3). However, the patent is silent about the enantiomeric purity of exametazime.

Scheme-3

KR615893B1 and its divisional patent KR632963B1 assigned to Dong A Pharm. Co. Ltd., discloses a method for the preparation of exametazime (Scheme 4) by avoiding the fractional crystallization step, the process involves condensation of dimethyl malonic acid with L-alanine methyl ester hydrochloride and D-alanine methyl ester hydrochloride to get corresponding stereoisomers, separately. Mixing equivalent moles of these stereoisomers and further reducing them to afford racemic mixture of amino alcohol intermediate. Protecting the nitrogen of amino alcohol intermediate followed by oxidation and Grignard reaction affords secondary alcohol intermediate, which on oxidation followed by condensation with hydroxylamine affords racemic mixture of nitrogen protected dioxime derivative. Deprotection of nitrogen affords exametazime.

Scheme-4

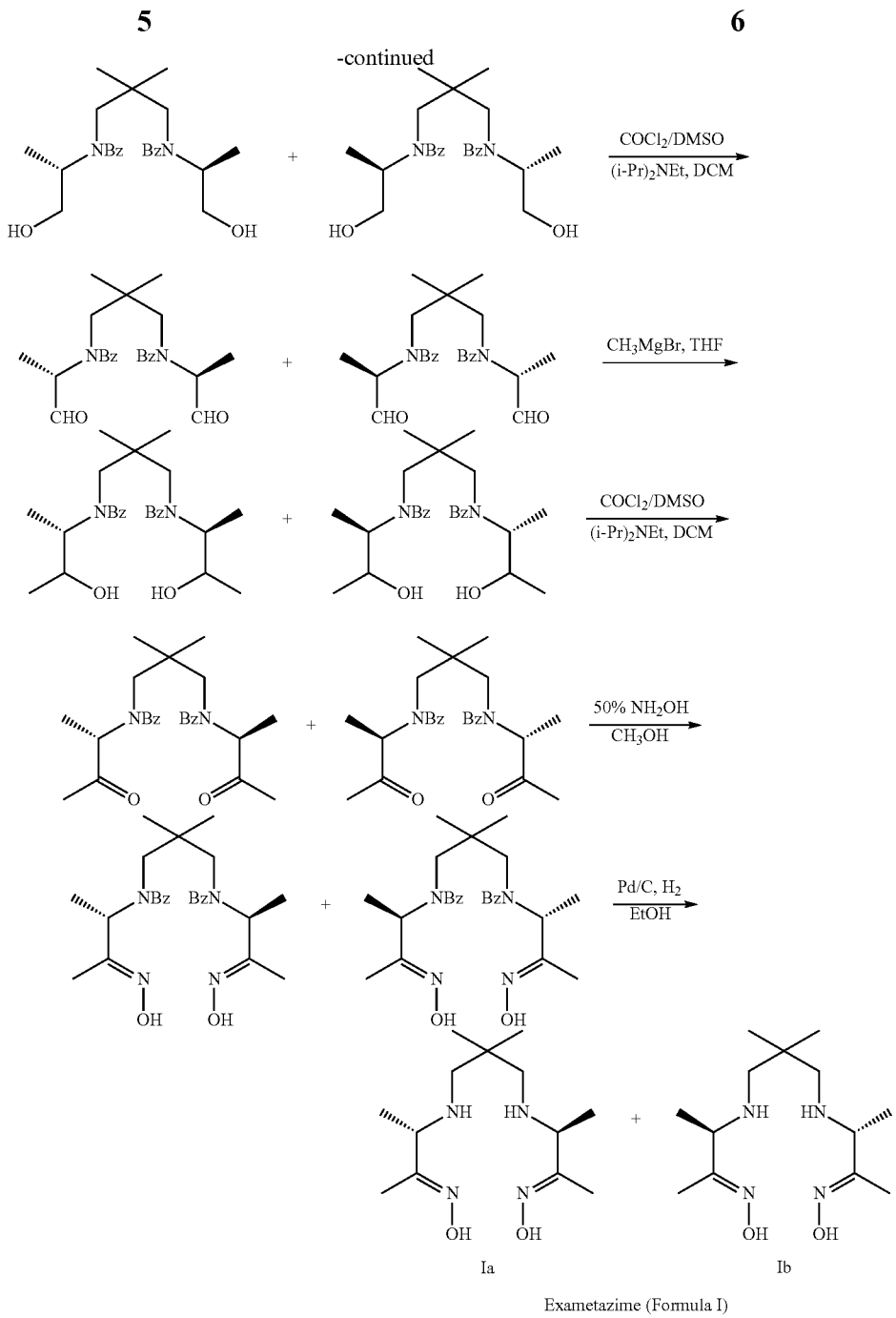

Exametazime (Formula I)

The process involves multiple steps, which in turn reduces the overall yield of exametazime. Chemical & Pharmaceutical Bulletin, Volume: 48, Issue: 2, Pages: 288-289, 2000, discloses one-pot procedure for the preparation of exametazime. The process involves reaction of 2,3-butanedione monoxime (formula II) with 2,2-dimethyl-1,3-propanediamine (formula III) in ethanol, followed by reduction with sodium borohydride to afford a mixture of 'd', 'l' and meso isomers. The said article discloses single recrystallization in ethyl acetate to afford a mixture of (70:30) dl and meso isomers. The known processes for the preparation of exametazime are not cost effective due to multiple recrystallizations, which is required for the removal of unwanted meso isomer from the racemic mixture of d and l isomers. The multiple recrystallizations reduce the overall yield of exametazime. The known processes also use benzene as solvent, which is carcinogenic.

Thus, there is a need to develop an alternative and improved process for the preparation of exametazime, which is simple, environment friendly, cost effective and improves the overall yield along with enantiomeric purity of exametazime.

SUMMARY OF THE INVENTION

In first aspect, the present application provides process for preparing exametazime (formula I),

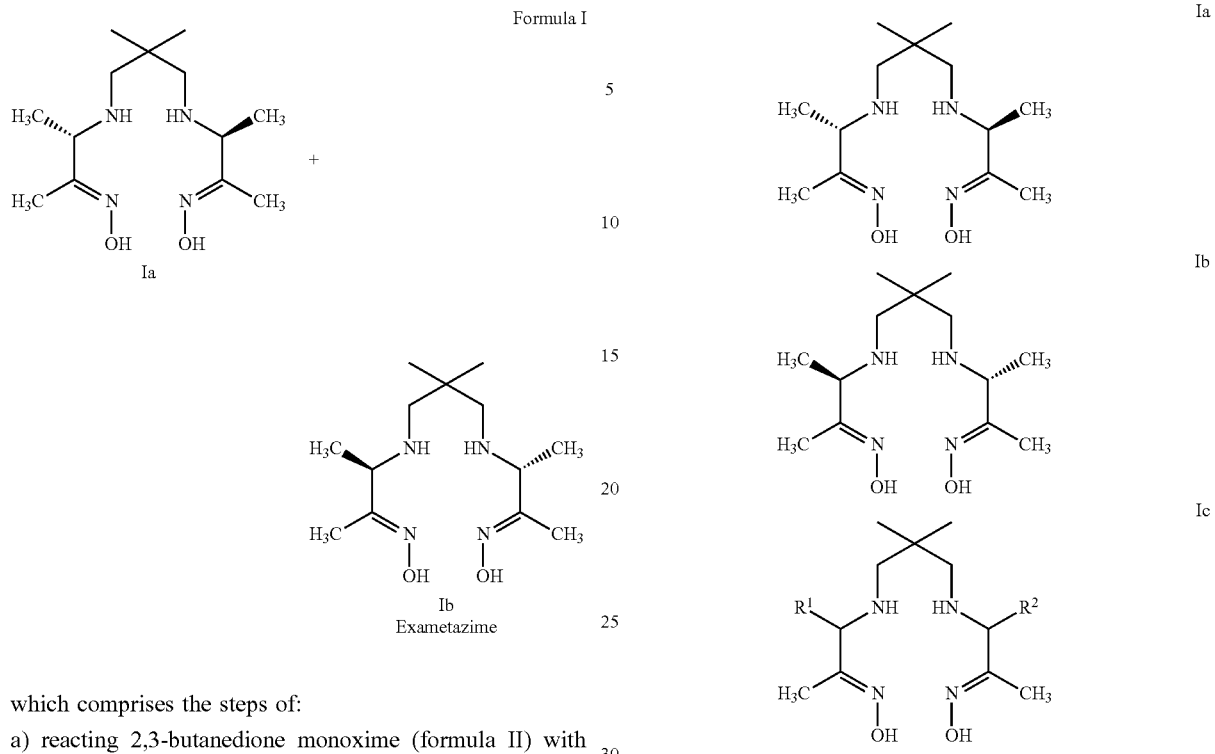

Formula I

Ia

Ib
Exametazime which comprises the steps of:

a) reacting 2,3-butanedione monoxime (formula II) with 2,2-dimethyl-1,3-propanediamine (formula III), in a suitable solvent, in presence of dehydrating agent to afford diimine derivative 4,8-diaza-3,6,6,9-tetramethylundecane-3,8-diene-2,10-dione bisoxime (formula IV),

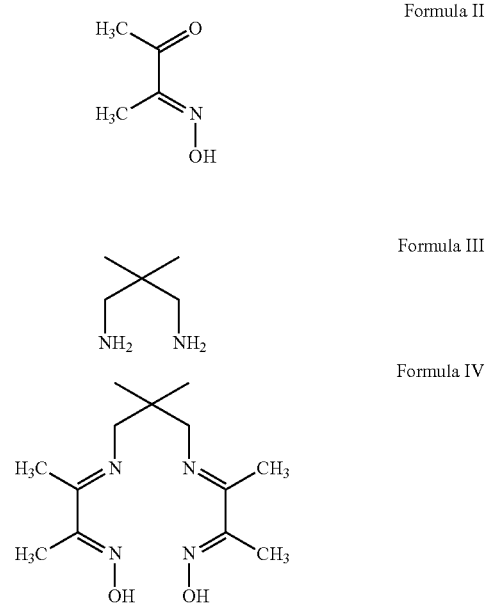

Formula II

Formula III

Formula IV b) reducing diimine derivative 4,8-diaza-3,6,6,9-tetramethylundecane-3,8-diene-2,10-dione bisoxime (formula IV) with a suitable reducing agent in a suitable solvent to afford a mixture of 'd', 'l' and meso isomers, c) optionally, purifying the mixture of 'd', 'l' and meso isomers, d) treating the mixture of 'd', 'l' and meso isomers with d or l chiral resolving acid to form the corresponding acid addition salts and separating said one of the enantiomers of exametazime as acid addition salt, e) optionally, purifying the acid addition salt obtained in step (d), f) treating the mother liquor of step (d) with a suitable base, g) isolating a mixture of 'd' or 'l' enantiomer and meso isomer, h) purifying the mixture obtained in step (g), i) treating the mixture from step (h) with l or d chiral resolving acid to form the corresponding acid addition salts and separating said other enantiomer of exametazime as an acid addition salt, j) optionally, purifying the acid addition salt obtained in step (i), k) mixing the acid addition salt of step (d) or (e) and step (i) or (j), l) optionally, purifying the mixture of acid addition salts obtained in step (k), m) treating the mixture of acid addition salts of step (k) or (l) with a suitable base to afford exametazime and, n) optionally, purifying the exametazime.

In second aspect, the present application provides process for preparing exametazime,

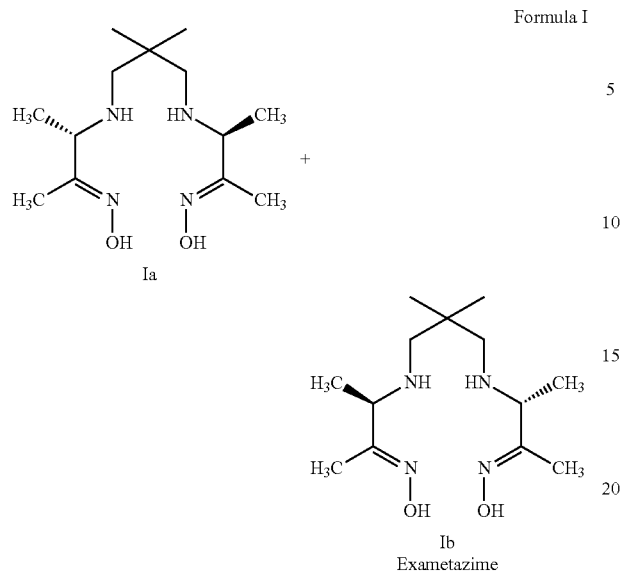

Formula I

Ia

Ib
Exametazime which comprises the steps of:

a) reacting 2,3-butanedione monoxime (formula II) with 2,2-dimethyl-1,3-propanediamine (formula III), in a suitable solvent, in presence of dehydrating agent to afford diimine derivative 4,8-diaza-3,6,6,9-tetramethylundecane-3,8-diene-2,10-dione bisoxime (formula IV),

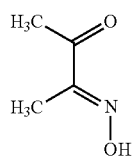

Formula II

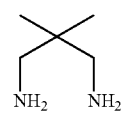

Formula III

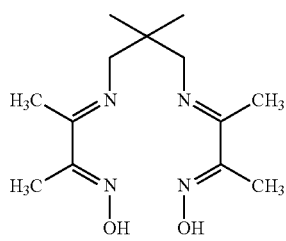

Formula IV b) reducing diimine derivative 4,8-diaza-3,6,6,9-tetramethylundecane-3,8-diene-2,10-dione bisoxime (formula IV) with a suitable reducing agent in a suitable solvent to afford a mixture of 'd', 'l' and meso isomers,

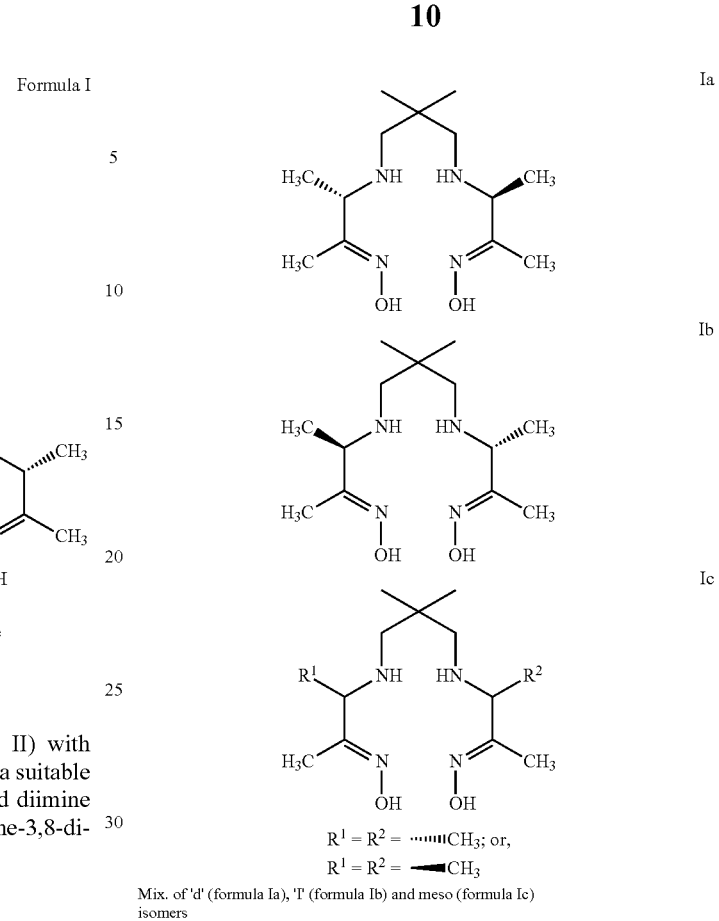

Ia

Ib

Ic $R^1 = R^2 =$ ⋯⋯$CH_3$; or,
$R^1 = R^2 =$ ━━$CH_3$

Mix. of 'd' (formula Ia), 'l' (formula Ib) and meso (formula Ic) isomers c) optionally, purifying the mixture of 'd', 'l' and meso isomers, d) treating the mixture of 'd', 'l' and meso isomers with d and l mixture of chiral resolving acid in a suitable solvent to afford acid addition salts and separating the acid addition salts of exametazime (d and l enantiomers), e) purifying the acid addition salts of exametazime (d and l enantiomers) obtained in step (d), f) treating the acid addition salts of exametazime with a suitable base to afford exametazime and, g) optionally purifying the exametazime.

DETAILED DESCRIPTION OF THE INVENTION

In first aspect (Scheme 5), the present application provides process for preparing exametazime (formula I), Formula I

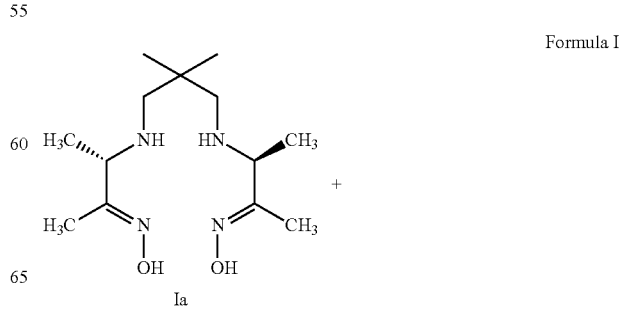

Ia

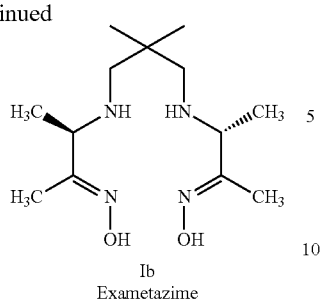

Ib
Exametazime which comprises the steps of:

a) reacting 2,3-butanedione monoxime (formula II) with 2,2-dimethyl-1,3-propanediamine (formula III), in a suitable solvent, in presence of dehydrating agent to afford diimine derivative 4,8-diaza-3,6,6,9-tetramethylundecane-3,8-diene-2,10-dione bisoxime (formula IV),

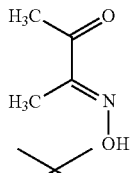

Formula II

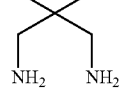

Formula III

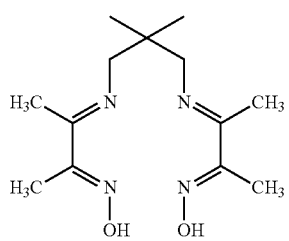

Formula IV b) reducing diimine derivative 4,8-diaza-3,6,6,9-tetramethylundecane-3,8-diene-2,10-dione bisoxime (formula IV) with a suitable reducing agent in a suitable solvent to afford a mixture of 'd', 'l' and meso isomers,

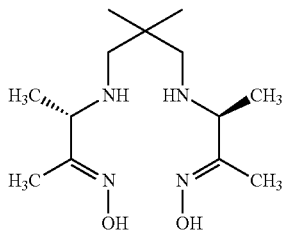

Ia

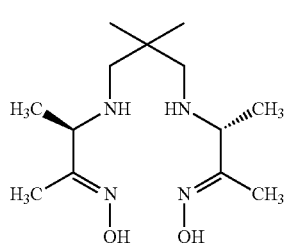

Ib

Ic $R^1 = R^2 = \text{''''''}CH_3$; or,
$R^1 = R^2 = \text{▬}CH_3$

Mix. of 'd' (formula Ia), 'l' (formula Ib) and meso (formula Ic) isomers c) optionally, purifying the mixture of 'l' and meso isomers, d) treating the mixture of 'd', 'l' and meso isomers with chiral resolving acid to form acid addition salts and separating one of the enantiomers of exametazime as acid addition salt, e) optionally, purifying the acid addition salt obtained in step (d), f) treating the mother liquor of step (d) with a suitable base, g) isolating a mixture of 'd' or 'l' enantiomer and meso isomer, h) purifying the mixture obtained in step (g), i) treating the mixture from step (h) with chiral resolving acid to form acid addition salts and separating other enantiomer of exametazime as an acid addition salt, j) optionally, purifying the acid addition salt obtained in step (i), k) mixing the acid addition salt of step (d) or (e) and step (i) or (j), l) optionally, purifying the mixture of acid addition salts obtained in step (k), m) treating the mixture of acid addition salts of step (k) or (l) with a suitable base to afford exametazime and, n) optionally, purifying the exametazime.

Scheme 5

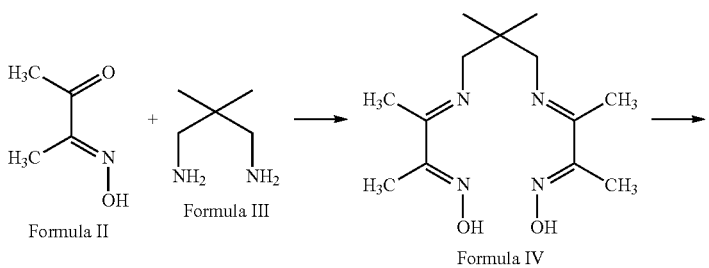

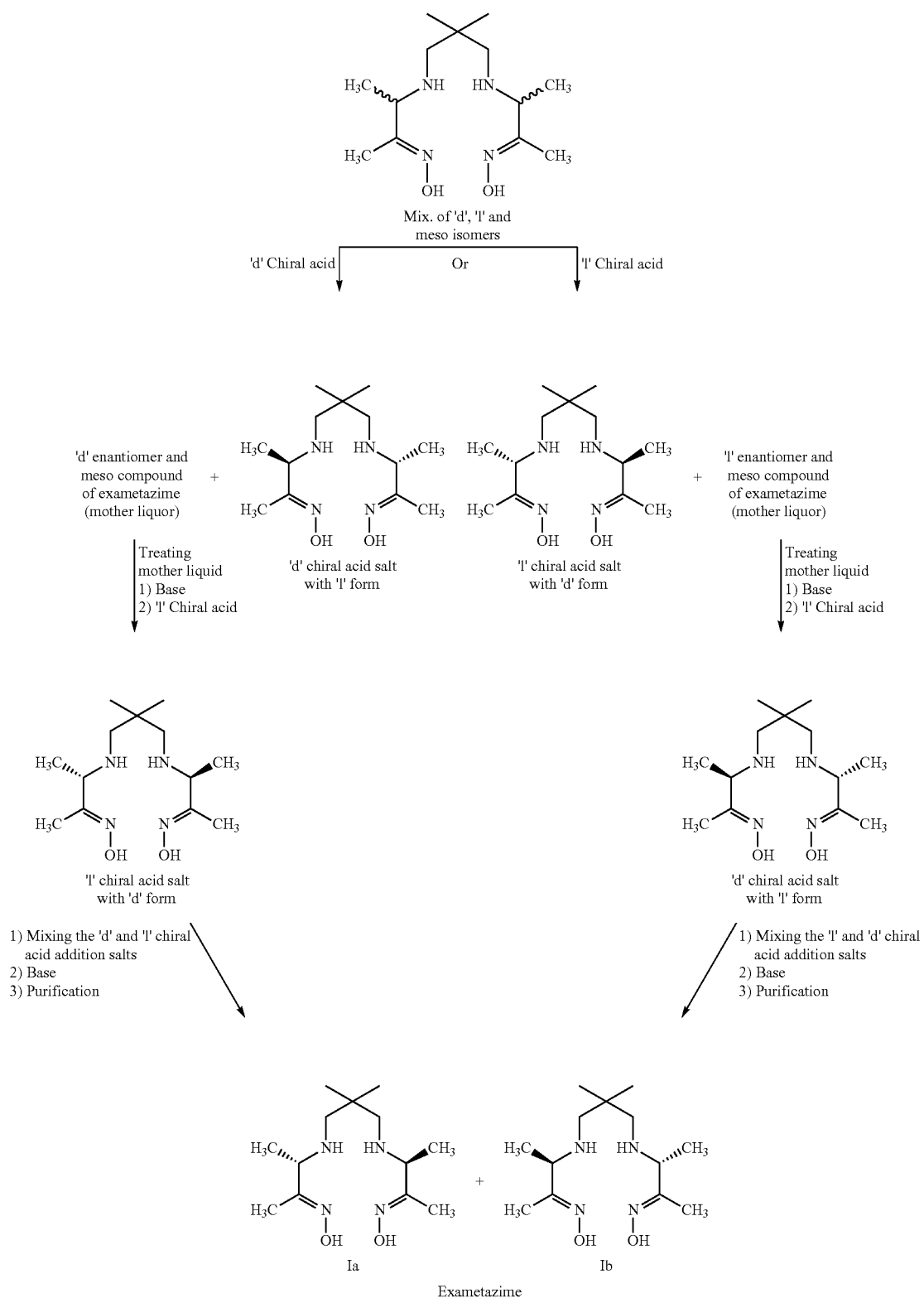

In second aspect (Scheme 6), the present application provides process for preparing exametazime,

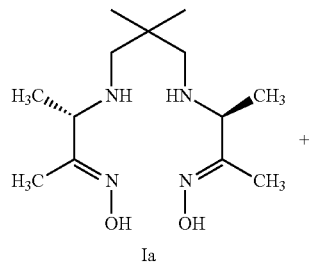
Ia

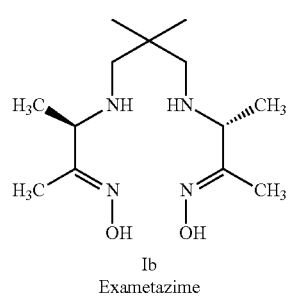
Ib
Exametazime which comprises the steps of:
a) reacting 2,3-butanedione monoxime (formula II) with 2,2-dimethyl-1,3-propanediamine (formula III), in a suitable solvent, in presence of dehydrating agent to afford diimine derivative 4,8-diaza-3,6,6,9-tetramethylundecane-3,8-diene-2,10-dione bisoxime (formula IV),

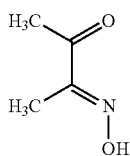

Formula II

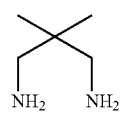

Formula III

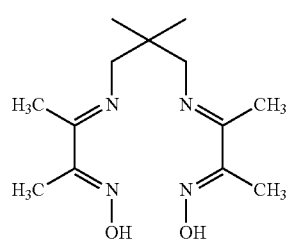

Formula IV b) reducing diimine derivative 4,8-diaza-3,6,6,9-tetramethylundecane-3,8-diene-2,10-dione bisoxime (formula IV) with a suitable reducing agent in a suitable solvent to afford a mixture of 'd', 'l' and meso isomers,

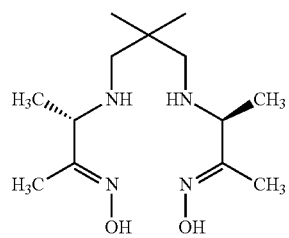
Ia

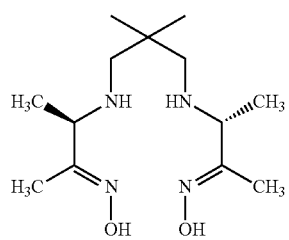
Ib

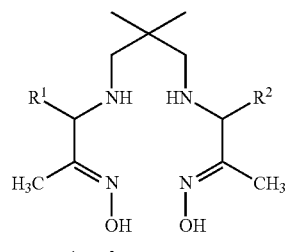
Ic $R^1 = R^2 = {\cdots}\text{ⅲCH}_3$; or,
$R^1 = R^2 = {-\!\!-}\text{CH}_3$ Mix. of 'd' (formula Ia), 'l' (formula Ib) and meso (formula Ic) isomers c) optionally, purifying the mixture of 'd', 'l' and meso isomers, d) treating the mixture of 'd', 'l' and meso isomers with d and l mixture of chiral resolving acid in a suitable solvent to afford acid addition salts and separating the acid addition salts of exametazime (d and l enantiomers), e) purifying the acid addition salts of exametazime (d and l enantiomers) obtained in step (d), f) treating the acid addition salts of exametazime with a suitable base to afford exametazime and, g) optionally purifying the exametazime.

Scheme 6

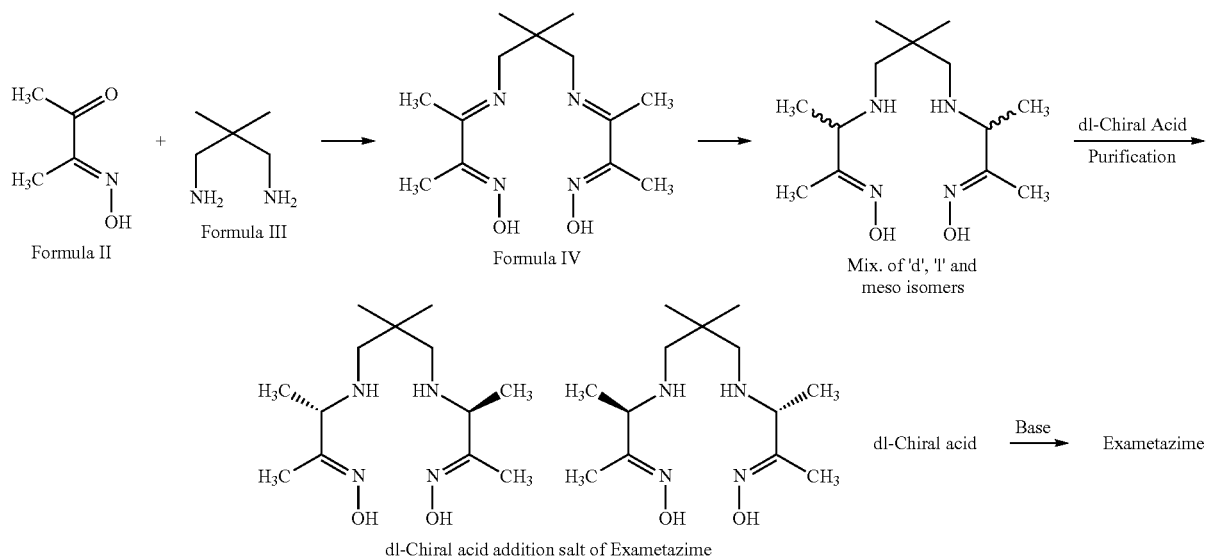

Step (a) of first and second aspects involve, reacting compound of formula II with the compound of formula III, in presence of dehydrating agent in a suitable solvent, to afford diimine derivative of compound of formula IV. The reaction of compound of formula II with the compound of formula III is carried out at suitable temperature, preferably at reflux temperature of solvent to achieve good yield and purity of compound of formula IV. The reaction can be completed in about 6 to 22 hours, preferably in about 10 to 18 hours. The completion of reaction can be monitored by any suitable technique such as high performance liquid chromatography (HLPC) or thin layer chromatography (TLC), gas chromatography (GC) and the like.

It is surprisingly found that the use of dehydrating agents during the reaction enhances the reaction rate and reduces the formation of the unwanted cyclic impurity referred below:

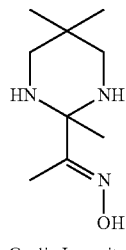

Cyclic Impurity

Suitable dehydrating agents that may be used in step (a) of first and second aspects include but are not limited to hydride such as calcium hydride. The dehydrating agents such as molecular sieves, anhydrous salts such as magnesium sulphate and sodium sulphate can as well be used.

The compound of formula III may be used either in its free base form or as its acid addition salt. Suitable acid addition salts include, but not limited to, salts with organic or inorganic acids.

The compound of formulas II and III can be prepared by any suitable methods known in the art preferably these can be prepared by the disclosed processes of patents viz. U.S. Pat. No. 4,789,736, U.S. Pat. No. 4,818,813 and EP0123504B1.

Step (b) of first and second aspects involve reduction of diimine derivative of compound of formula IV with a suitable reducing agent in a suitable solvent to afford a mixture of 'l' and meso isomers, which may optionally be purified to achieve higher chemical purity.

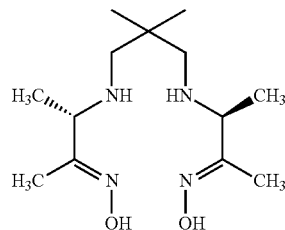

Ia

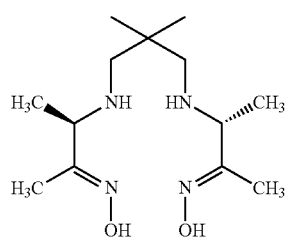

Ib

-continued

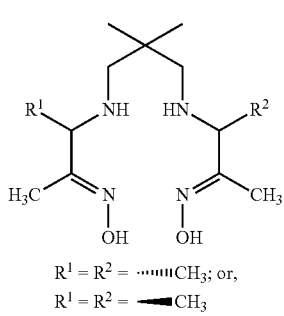

Ic

R¹ = R² = ·······ıııCH₃; or,
R¹ = R² = ◂▬CH₃

Mix. of 'd' (formula Ia), 'l' (formula Ib) and meso (formula Ic) isomers

The reduction of compound of formula IV is carried out at any suitable temperature preferably at about 0° C. to about 30° C., more preferably at about 5° C. to about 20° C. The reduction can be completed in about 10 to 22 hours, preferably in about 12 to 18 hours. The completion of reaction can be monitored by any suitable technique such as high performance liquid chromatography (HLPC) or thin layer chromatography (TLC), gas chromatography (GC) and the like.

Suitable reducing agent that may be used in step (b) of first and second aspects include but are not limited to borohydride reagents (e.g., sodium borohydride, sodium cyanoborohydride) and sodium triacetoxyborohydride and the like.

The reaction mixture obtained from step (a) and step (b) of first and second aspects may be optionally processed to remove any insoluble solids, and particles by methods such as decantation, centrifugation, gravity filtration, suction filtration, or any other techniques for the removal of solids.

The products of step (a) and step (b) of first and second aspects may be isolated directly from the reaction mixture itself after the reaction is complete in step (a) and step (b) of first and second aspects, or after conventional work up with techniques such as filtration, quenching with a suitable reagent, extraction, or the like. Optionally, the crude product of steps (a) and (b) of first and second aspects may be directly used for next step or it may be isolated as a solid. The isolation of the step (a) and step (b) products of first and second aspects may involve methods including removal of solvent, cooling, concentrating the reaction mass, adding an anti-solvent, extraction with a solvent, and the like. The other alternate methods, such as for example, shaking, agitation, and the like, may also be employed for isolation.

Further, the resulting compound of formula IV of step (a) and mixture of 'd', 'l' and meso isomers of step (b) of first and second aspects may be further purified by recrystallization, slurrying in a suitable solvent, treating with adsorbent materials such as, but not limited to, silica gel, aluminium oxide, synthetic resin, and the like; or any other suitable techniques.

The purified mixture of 'd', 'l' and meso isomers of first and second aspects may be in the form of a crystalline compound, a solvate, an amorphous compound, or a mixture thereof. The solid may be optionally further dried. Drying may be suitably carried out using a tray dryer, vacuum oven, air oven, fluidized bed dryer, spin flash dryer, flash dryer, and the like, at atmospheric pressure or at any suitable temperature or under reduced pressure and in the presence or absence of an inert atmosphere, such as nitrogen, argon, neon, or helium. The drying may be carried out for desired time periods to achieve the desired quality of the mixture of 'd', 'l' and meso isomers.

Suitable solvents that may be used in steps (a) and (b) of first and second aspects and/or for purification of compound of formula IV and mixture of 'd', 'l' and meso isomers of first and second aspects include but not limited to nitriles, alcohols in presence or absence of water, esters, halogenated hydrocarbons, ethers, amides, dialkylsulfoxides, hydrocarbons, or the mixtures thereof. Nitriles are selected from the group comprising of acetonitrile, propionitrile, butyronitrile, valeronitrile and the like. Alcohols are selected from the group comprising of methanol, ethanol, n-propanol, isopropanol, n-butanol, and the like, or their aqueous solutions. Esters are selected from the group comprising of ethyl acetate, propyl acetate, isopropyl acetate, butyl acetate and the like. Halogenated hydrocarbons are selected from the group comprising of dichloromethane (DCM), chloroform, dichloroethane, chlorobenzene and the like. Ethers are selected from the group comprising of diethyl ether, methyl tert-butyl ether (MTBE), diisopropyl ether, tetrahydrofuran (THF), dioxane and the like. Amides are selected from the group comprising of N,N-dimethylformamide (DMF), N,N-dimethylacetamide (DMA), N-methylformamide, N-methylpyrrolidone and the like. Dialkyl sulfoxides can be selected from the group comprising of dimethylsulfoxide, diethylsulfoxide, dibutylsulfoxide and the like. Aliphatic hydrocarbons are selected from the group comprising of alkanes or cycloalkanes such as pentane, hexane, heptane, octane, cyclohexane, cyclopentane and the like. Aromatic hydrocarbons are selected from the group comprising of toluene, xylene and the like. Proviso that ketones/nitriles are not used during the reduction reaction of step (b); and water is avoided in condensation step (a) however it may be used in step (b) of first and second aspects.

The use of anhydrous alcohols or their aqueous solution is preferred in reduction step (b) of first and second aspects, however it is advantageous to use anhydrous alcohols to improve d and l content in the isolated material of step (b).

Optionally the steps (a) and (b) of first and second aspects may be carried out in-situ, i.e. without isolating the intermediates formed in one or more stages.

In step (d) of first aspect, the person skilled in the art may utilize either 'd' or 'l' isomer of chiral resolving acid to isolate corresponding enantiomer of exametazime from a mixture of 'd', 'l' and meso isomers of step (b) or (c) of first aspect. Accordingly, in step (i) of first aspect, the appropriate isomer of chiral resolving acid can be utilized to isolate second enantiomer of exametazime from the second mixture of or 'l' and meso isomers of step (h) of first aspect.

In general, the preparation of acid addition salts in step (d) and in step (i) of first aspect can be achieved by reacting the corresponding chiral resolving acid with the material obtained from steps (b) or (c) and step (h) of first aspect. The reaction can be performed in any suitable solvent and preferably it can be carried out at any suitable temperature such as at about 0° C. to about 40° C. or at reflux temperature of the solvent. The reaction can be completed in about 2 to 15 hours, preferably in about 4 to 10 hours.

The appropriate suitable chiral resolving acid that may be used in step (d) and in step (i) of first aspect can be selected from, but not limited to L-(+) tartaric acid, D-(−) tartaric acid, L-malic acid, D-malic acid, S-(+) mandelic acid, R-(−) mandelic acid, S-(+)-O-acetyl mandelic acid, R-(−)-O-acetyl mandelic acid, (−)-naproxen, (+)-naproxen, (1R)-(−)-camphor sulfonic acid, (1S)-(+)-camphor sulfonic acid, (1R)-(+)-bromocamphor-10-sulfonic acid, (1 S)-(−)-bromocamphor-10-sulfonic acid, (−)-Dibenzoyl-L-tartaric acid, (−)-Dibenzoyl-L-tartaric acid monohydrate, (+)-Dibenzoyl-D-tartaric acid, (+)-Dibenzoyl-D-tartaric acid monohydrate, (+)-dipara-tolyl-D-tataric acid, (−)-dipara-tolyl-L-tataricacid, L(−)-pyroglutamic acid, L(+)-pyroglutamic acid, (+)-lactic acid, (−)-lactic acid, (S)-(+)-2-chloromandelic acid, (R)-(−)-2-chloromandelic acid; preferably L-(+) tartaric acid and D-(−) tartaric acid.

The isomeric mixture of 'd' or 'l' and meso isomers of step (g) of first aspect can be isolated by treating the mother liquor of step (d) of first aspect with a suitable base, preferably the volume of mother liquor is reduced by any suitable techniques such as concentrating the solution prior to neutralization reaction with a base. The neutralization reaction can be performed at about 5° C. to 30° C. by adjusting the pH about 9-10 with a suitable base.

The resulting acid addition salts of steps (d) and (i) of first aspect and the precipitated solid of 'd' or 'l' and meso isomers of step (g) of first aspect may be further purified by recrystallization, slurrying in a suitable solvent, treating with adsorbent materials such as, but not limited to, silica gel, aluminium oxide, synthetic resin, and the like; or any other suitable techniques.

Suitable solvents that may be used in steps (d) and (i) of first aspect and/or for purification of acid addition salts of steps (e) and (j); and precipitated solid of 'd' or 'l' and meso isomers of step (h) of first aspect include but not limited to nitriles, alcohols in presence or absence of water, ketones, esters, halogenated hydrocarbons, ethers, amides, dialkyl-sulfoxides, hydrocarbons or mixtures thereof or their mixtures with water. Nitriles are selected from the group comprising of acetonitrile, propionitrile, butyronitrile, valeronitrile and the like. Alcohols are selected from the group comprising of methanol, ethanol, n-propanol, isopropanol, n-butanol, and the like or their aqueous solutions. Ketones are selected from the group comprising of acetone, methyl ethyl ketone, methyl isobutyl ketone and the like. Esters are selected from the group comprising of ethyl acetate, propyl acetate, isopropyl acetate, butyl acetate and the like. Halogenated hydrocarbons are selected from the group comprising of dichloromethane (DCM), chloroform, dichloroethane, chlorobenzene and the like. Ethers are selected from the group comprising of diethyl ether, methyl tert-butyl ether (MTBE), diisopropyl ether, tetrahydrofuran (THF), dioxane and the like. Amides are selected from the group comprising of N,N-dimethylformamide (DMF), N,N-dimethylacetamide (DMA), N-methylformamide, N-methylpyrrolidone and the like. Dialkyl sulfoxides can be selected from the group comprising of dimethylsulfoxide, diethylsulfoxide, dibutylsulfoxide and the like. Aliphatic hydrocarbons are selected from the group comprising of alkanes or cycloalkanes such as pentane, hexane, heptane, octane, cyclohexane, cyclopentane and the like. Aromatic hydrocarbons are selected from the group comprising of toluene, xylene and the like.

It is surprisingly found that the use of alcohols or their aqueous solution during the acid addition salts preparation, in step (d) of first and second aspects and step (i) of first aspect, reduces the content of meso isomer in precipitated acid addition salts, so effectively, that it may not require any further purification step for the removal of meso isomer. Moreover, the use of alcohols or their aqueous solution during the purification of acid addition salts in step (e) of first and second aspects, and step (j) of first aspect effectively reduces the content of meso isomer.

Preferably, the percentage of aqueous alcohol may range from 3% to 15% by volume, more preferably from 5% to 10% by volume.

The use of ethyl acetate is preferred for the purification of a mixture of or 'l' enantiomer and meso isomer in step (h) of first aspect, as it produces the corresponding 'd' or 'l' enriched mixture.

In a preferred method of first aspect, the mixture of 'd', 'l' and meso isomers of step (d) is treated with L-(+)-tartaric acid at reflux temperature of ethanol for about 1-6 hours to precipitate L-(+)-tartrate salt of compound of formula Ib, which is optionally further purified with a suitable technique.

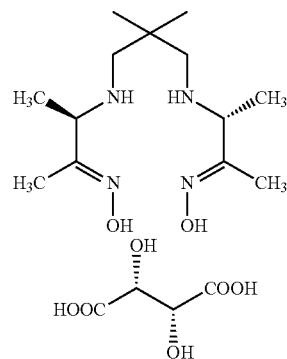

L-(+)-tartrate salt of formula Ib

The filtrate of step (d) of first aspect contains an isomeric mixture of formula Ia, formula Ic (meso isomer) as L-(+)-tartaric acid salt. The said acid of the mixture is neutralized by adjusting the pH about 9-10 with an aqueous solution of base, the precipitated solid is purified with ethyl acetate. The solid isolated from the filtrate is an isomeric mixture of formula Ia and formula Ic (meso isomer),

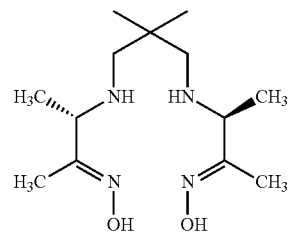

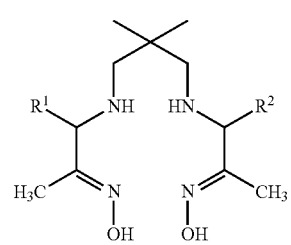

$R^1 = R^2 = \cdots\cdots\text{CH}_3$; or,
$R^1 = R^2 = \text{—CH}_3$

Mixture of formula Ia, and meso (formula Ic) isomers

The solid of isomeric mixture is further added to ethanol and treated with D-(−)-tartaric acid at reflux temperature of ethanol for about 1-6 hours to precipitate, D-(−)-tartrate salt of compound of formula Ia, which is optionally further purified with a suitable technique.

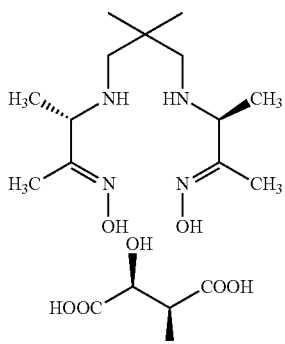

D-(−)-tartrate salt of formula Ia

Step (k) of first aspect involves, mixing the acid addition salt of step (d) or (e) and step (i) or (j), the said mixture is optionally purified prior to acid neutralization reaction with a suitable technique. The acid neutralization reaction can be performed at about 5° C. to 30° C. by adjusting the pH about 9-10 with a suitable base to isolate exametazime, which may further purified to afford pure exametazime. In second aspect of present application, the step (d) involve treating the mixture of 'd', 'l' and meso isomers of step (b) or (c) of second aspect with d and l mixture of chiral resolving acid in a suitable solvent to afford acid addition salts of exametazime, which is preferably dl-tartrate salts of exametazime,

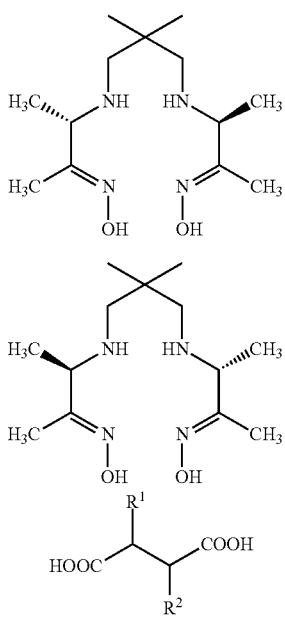

di-tartrate salt of Exametazime

The reaction is carried out at any suitable temperature such as at about 0° C. to about 60° C. or at reflux temperature of the solvent. The reaction can be completed in about 2 to 15 hours, more preferably in about 4 to 10 hours.

Suitable and 'l' mixture of chiral resolving acid that may be used in step (d) of second aspect is (±) tartaric acid, (±) malic acid, (±) ascorbic acid, (±) mandelic acid, (±)-O-acetyl mandelic acid, (±) naproxen, (±) camphor sulfonic acid, (±) bromocamphor-10-sulfonic acid, (±) Dibenzoyl-tartaric acid, (±) dipara-tolyl-tataric acid, (±) pyroglutamic acid, (±) lactic acid, (±)-2-chloromandelic acid, preferably (±) tartaric acid.

The resulting and 'l' mixture of chiral resolving acid addition salts of exametazime is further purified by recrystallization, slurrying in a suitable solvent, treating with adsorbent materials such as, but not limited to, silica gel, aluminium oxide, synthetic resin, and the like; or any other suitable techniques.

The step (f) of second aspect involves, treating 'd' and 'l' mixture of chiral resolving acid salts of exametazime with a suitable base. The acid neutralization reaction can be performed at about 5° C. to 30° C. by adjusting the pH about 9-10 with a suitable base to isolate crude exametazime, which may further purified to afford pure exametazime.

Suitable bases that may be used for neutralization reaction in step (f) of first and second aspects and step (m) of first aspect include and are not limited to: inorganic bases, such as, for example, sodium hydroxide, potassium hydroxide, sodium carbonate, potassium carbonate, sodium bicarbonate, potassium bicarbonate, and the like, either alone or as their aqueous solutions.

The mixture of acid additions salts of step (k) of first aspect, and crude exametazime obtained from first and second aspects may be further purified by recrystallization, slurrying in a suitable solvent, treating with adsorbent materials such as, but not limited to, silica gel, aluminium oxide, synthetic resin, and the like; or any other suitable techniques.

Suitable solvents that may be used in step (d) of second aspect and purification of acid addition salts of step (l) of first aspect, chiral resolving acid addition salts of exametazime of step (e) of second aspect and crude exametazime include but not limited to nitriles, alcohols in presence or absence of water, ketones, esters, halogenated hydrocarbons, ethers, amides, dialkylsulfoxides, hydrocarbons or mixtures thereof or their mixtures with water. Nitriles are selected from the group comprising of acetonitrile, propionitrile, butyronitrile, valeronitrile and the like. Alcohols are selected from the group comprising of methanol, ethanol, n-propanol, isopropanol, n-butanol, and the like or their aqueous solutions. Ketones are selected from the group comprising of acetone, methyl ethyl ketone, methyl isobutyl ketone and the like. Esters are selected from the group comprising of ethyl acetate, propyl acetate, isopropyl acetate, butyl acetate and the like. Halogenated hydrocarbons are selected from the group comprising of dichloromethane (DCM), chloroform, dichloroethane, chlorobenzene and the like. Ethers are selected from the group comprising of diethyl ether, methyl tert-butyl ether (MTBE), diisopropyl ether, tetrahydrofuran (THF), dioxane and the like. Amides are selected from the group comprising of N,N-dimethylformamide (DMF), N,N-dimethylacetamide (DMA), N-methylformamide, N-methylpyrrolidone and the like. Dialkyl sulfoxides can be selected from the group comprising of dimethylsulfoxide, diethylsulfoxide, dibutylsulfoxide and the like. Aliphatic hydrocarbons are selected from the group comprising of alkanes or cycloalkanes such as pentane, hexane, heptane, octane, cyclohexane, cyclopentane and the like. Aromatic hydrocarbons are selected from the group comprising of toluene, xylene and the like.

The reaction mixture obtained in step (m) of first aspect and step (f) of second aspect may optionally be processed to remove any insoluble solids or particles by methods such as decantation, centrifugation, gravity filtration, suction filtration, or any other technique for the removal of solids.

The product so obtained may be isolated as a solid directly from the reaction mixture after the reaction is complete in step (m) of first aspect and step (f) of second aspect, or after conventional work up; by techniques such as filtration, quenching with a suitable reagent, extraction, and the like. The said isolation may include removal of solvent, cooling, concentrating the reaction mass, adding an anti-solvent, extraction with a solvent, or the like. The other alternate methods, such as for example, shaking, agitation, and the like, may also be employed for isolation.

The product exametazime thus obtained from first and second aspects may be recovered as solid using conventional methods including decantation, centrifugation, gravity filtration, suction filtration, or other techniques known in the art. The resulting compound may be in the form of a crystalline compound, a solvate, an amorphous compound, or a mixture thereof. The solid may be optionally further dried.

All percentages and ratios used herein are by weight of the total composition and all measurements made are at about 25° C. and about atmospheric pressure, unless otherwise designated. All temperatures are in degrees Celsius unless specified otherwise. As used herein, "comprising" means the elements recited, or their equivalents in structure or function, plus any other element or elements which are not recited. The terms "having" and "including" are also to be construed as open ended. All ranges recited herein include the endpoints, including those that recite a range "between" two values. Whether so indicated or not, all values recited herein are approximate as defined by the circumstances, including the degree of expected experimental error, technique error, and instrument error for a given technique used to measure a value.

Certain specific aspects and embodiments of the present application will be explained in greater detail with reference to the following examples, which are provided only for purposes of illustration and should not be construed as limiting the scope of the disclosure in any manner. Reasonable variations of the described procedures are intended to be within the scope of the present application. While particular aspects of the present application have been illustrated and described, it would be apparent to those skilled in the art that various other changes and modifications can be made without departing from the spirit and scope of the disclosure. It is therefore intended to encompass all such changes and modifications that are within the scope of this disclosure.

EXAMPLES

Example 1

Preparation of Exametazime 'Formula I' Involving the Separate Use of d & l Tartaric Acid with Purification of Corresponding Distereomeric Salts: Method A Step I: Preparation of Diimine Derivative 4,8-diaza-3,6,6,9-tetramethylundecane-3,8-diene-2,10-dione bisoxime (Formula IV)

To a cooled (0-5° C.) solution of 2,3-butanedione monoxime (formula II; 118.6 g) and 2,2-dimethyl-1,3-propanediamine (formula III; 50.0 g) in acetonitrile (500 mL), was added calcium hydride (42.0 g) portionwise and solution was stirred at 0-5° C. for next 30 minutes and then allowed to warm to room temperature. The solution was slowly brought to reflux and kept under stirring at the same temperature for ~6-10 hours. The reaction mixture was cooled ~70° C., filtered through celite and washed with acetonitrile (200 mL). The filtrate was concentrated under vacuum and the obtained solid residue was crystallized in acetonitrile (150 mL) to afford the title compound (Weight: 66.0 g; Yield: 50.26%).

Step II: Preparation of a Mixture of 'd', 'l' and Meso Isomers

To the cooled (0° C.) suspension of diimine derivative (formula IV; 66.0 g) in ethanol, sodium borohydride (18.63 g) was added portionwise at 0-5° C. in 30 minutes and kept stirring at this temperature for 30 minutes. The reaction mass was concentrated under vacuum and then diluted with water (198 mL). The resulting suspended mass was stirred at 5-10° C. for 16 hours and solid was filtered which was stirred under reflux in ethyl acetate (1800 mL) and filtered off the undissolved residue through celite. The filtrate was concentrated to afford the title compound as a white solid (Weight: 32.0 g; Yield: 48%; Chiral Purity: d-isomer ~23%, l-isomer ~23%, meso-isomer ~54%).

Step III: Preparation of L-(+)-Tartrate Salt of Compound of Formula Ib

L-(+)-Tartaric acid (16.8 g) was added to a suspended mixture of 'd', 'l' and meso isomers (30.5 g) in ethanol (915 mL). The resulting mixture was stirred under reflux for 2 hours, cooled to 25-30° C. in 2-3 hours and kept stirring at this temperature for another 3 hours. The solid was filtered, washed with ethanol (15 mL) at 25-30° C. and dried at 40-45° C. under vacuum to afford the title compound (Weight: 11.0 g; Yield: 23.25%; Chiral Purity: l-isomer ~96%, meso-isomer ~4%, d-isomer 0%).

Step IV: Purification of L-(+)-Tartrate Salt of Compound of Formula Ib

A suspension of L-(+)-tartrate salt of compound of formula Ib (11.0 g) in 5% aqueous ethanol (220 mL) was stirred under reflux for 2 hours. It was gradually cooled to 25-30° C. in 3-4 hours and stirred at this temperature for another 3 hours. The solid was filtered, washed with ethanol (5.5 mL) at 25-30° C. and dried at 45-50° C. under vacuum to afford pure L-(+)-tartrate salt of compound of formula Ib (Weight: 8.0 g; Yield: 72.72%; Chiral Purity: l-isomer 99.85%, meso-isomer ~0.15%, d-isomer 0%).

Step V: Isolation of Isomeric Mixture of Formula Ia and Formula Ic (Meso Isomer)

The filtrate of step III (method A) above, was concentrated under vacuum at 40-45° C. and traces of ethanol was removed by chasing with ethyl acetate (50 mL). The obtained residue was dissolved in water (27.0 mL) and pH was adjusted to ~10 with 20% aqueous sodium hydroxide solution (35 mL) at 10-15° C. The suspended solution was stirred at 10-15° C. for 2 hours, filtered the solid under vacuum and washed with cold (10-15° C.) water (20 mL). The solid was dried at 45-50° C. then suspended in ethyl acetate (1250 mL) which was stirred under reflux for 2 hours and cooled to room temperature and stirred for another 3 hours. The undissolved solid residue was filtered off and washed the solid residue with ethyl acetate (50.0 mL). The filtrate was concentrated under vacuum to afford the title compound (Weight: 12.0 g; Chiral Purity: d-isomer ~57%, meso-isomer ~43%, l-isomer ~0%)

Step VI: Preparation of D-(−)-Tartrate Salt of Compound of Formula Ia

D-(−)-tartaric acid (6.61 g) was added to a suspension of isomeric mixture of formula Ia, formula Ic (meso isomer) (12.0 g) in ethanol (180 mL) and stirred under reflux for 2 hours. Reaction mass was cooled to 25-30° C. in 2-3 hours and stirred at this temperature for 3 hours. The solid was filtered, washed with ethanol (12 mL) at 25-30° C. and dried at 40-45° C. under vacuum to afford the title compound (Weight: 10.5 g; Yield: 56.45%; Chiral Purity: d-isomer ~97.6%, l-isomer 0%, meso-isomer ~2.5%).

Step VII: Purification of D-(−)-Tartrate Salt of Compound of Formula Ia

The D-(−)-tartrate salt of compound of formula Ia (10.5 g) was suspended in 5% aqueous ethanol (157.5 mL) heated to reflux for 2 hours and gradually cooled to 25-30° C. in 3-4 hours. Reaction mass was stirred at 25-30° C. for 3 hours. The solid was filtered and washed with ethanol (5 mL) at 25-30° C. The solid was dried at 45-50° C. under vacuum to afford the title compound (Weight: 8.65 g; Yield: 82.38%; Chiral Purity: d-isomer 99.67%, l-isomer 0%, meso isomer ~0.33%).

Step VIII: Preparation of Exametazime (Formula I)

To a cooled (10-15° C.) solution of pure L-(+)-tartrate salt of compound of formula Ib (8.0 g) and pure D-(−)-tartrate salt of compound of formula Ia (8.0 g) in water (10 mL) was added 20% aqueous sodium hydroxide solution (15 mL) to adjust its pH to ~10 and stirred for 2 hours at 10-15° C. The solid was filtered and washed with cold (10-15° C.) water. The solid was dried at 45-50° C. which was suspended in ethyl acetate (470 mL) and stirred under reflux for 2 hours. The undissolved solid was filtered off through micron. The filtrate was concentrated under vacuum to provide white solid mass which was dissolved in ethyl acetate (50 mL) under reflux, stirred for 2 hours. The solution was cooled to 25-30° C. and stirred for 16-18 hours. The precipitated solid was filtered and dried under vacuum at 40-45° C. to afford exametazime of formula I (Weight: 7.0 g; Yield: 67.96%; Chiral Purity: d-isomer ~48.5%, l-isomer 51.4%, meso-isomer Not detected).

Example 2

Preparation of Exametazime 'Formula I' Involving the Separate Use of d & l Tartaric Acid and without Separate Purification of Corresponding Distereomeric Salts: Method B Step I: Preparation of Diimine Derivative 4,8-diaza-3,6,6,9-tetramethylundecane-3,8-diene-2,10-dione bisoxime (Formula IV)

To a cooled (0-5° C.) solution of 2,3-butanedione monoxime (formula II; 118.6 g) and 2,2-dimethyl-1,3-propanediamine (formula III; 50.0 g) in acetonitrile (500 mL), was added calcium hydride (42.0 g) portionwise and solution was stirred at 0-5° C. for next 30 minutes and then allowed to warm to room temperature. The solution was slowly brought to reflux and kept under stirring at the same temperature for ~6-10 hours. The reaction mixture was cooled ~70° C., filtered through celite and washed with acetonitrile (200 mL). The filtrate was concentrated under vacuum to afford the title compound as an oily residue (Weight: 130.0 g; Yield: 99.23%).

Step II: Preparation of a Mixture of 'd', 'l' and Meso Isomers

To the cooled (0° C.) suspension of diimine derivative (formula IV; 130.0 g) in ethanol (750 mL), sodium borohydride (18.63 g) was added portionwise at 0-5° C. in 60 minutes and kept stirring at this temperature for 30 minutes. The reaction mass was concentrated under vacuum and then diluted with water (250 mL). The resulting suspended reaction mass was stirred at 5-10° C. for 16 hours and solid was filtered which was stirred under reflux in ethyl acetate (1800 mL) and filtered off the undissolved residue through celite. The filtrate was concentrated under vacuum at 40-45° C. to afford a white solid, which was recrystallized in acetonitrile at −10 to −20° C. to afford the title compound (Weight: 64.0 g; Yield: 48.74% (from step I); Chiral Purity: d-isomer ~24%, l-isomer ~24%, meso-isomer ~52%).

Step III: Preparation of L-(+)-Tartrate Salt of Compound of Formula Ib

L-(+)-Tartaric acid (34.7 g) was added to a suspended mixture of 'd', 'l' and meso isomers (63 g) in ethanol (1890 mL). The resulting mixture was stirred under reflux for 2 hours, cooled to 25-30° C. in 2-3 hours and kept stirring at this temperature for another 3 hours. The solid was filtered, washed with ethanol (25 mL) at 25-30° C. and dried at 40-45° C. under vacuum to afford the title compound (Weight: 25.0 g; Yield: 25.57%; Chiral Purity: l-isomer ~93%, meso-isomer ~6.1%, d-isomer 0.59%).

Step IV: Isolation of Isomeric Mixture of Formula Ia and Formula Ic (Meso Isomer)

The filtrate of step III (method B) above was concentrated under vacuum at 40-45° C. and traces of ethanol was removed by chasing with ethyl acetate (50 mL). The obtained residue was dissolved in water (63.0 mL) and pH was adjusted to −10 with 20% aqueous sodium hydroxide solution (74 mL) at 10-15° C. The suspended solution was stirred at 10-15° C. for 2 hours, filtered the solid under vacuum and washed with cold (10-15° C.) water (20 mL). The solid was dried at 45-50° C. then suspended in ethyl acetate (2750 mL) which was stirred under reflux for 2 hours and cooled to room temperature and stirred for another 3 hours. The undissolved solid residue was filtered off and washed the solid residue with ethyl acetate (25.0 mL). The filtrate was concentrated under vacuum to afford the title compound (Weight: 25.0 g; Chiral Purity: d-isomer ~58%, meso-isomer ~42%, l-isomer ~0%).

Step V: Preparation of D-(−)-Tartrate Salt of Compound of Formula Ia

D-(−)-tartaric acid (13.23 g) was added to a suspension of isomeric mixture of formula Ia, formula Ic (meso isomer) (24.0 g) in ethanol (360 mL) and stirred under reflux for 2 hours. Reaction mass was cooled to 25-30° C. in 2-3 hours and stirred at this temperature for 3 hours. The solid was filtered, washed with ethanol (24 mL) at 25-30° C. and dried at 40-45° C. under vacuum to afford the title compound (Weight: 20.5 g; Yield: 55.1%; Chiral Purity: d-isomer ~97.7%, l-isomer 0%, meso-isomer ~2.27%).

Step VI: Preparation of Exametazime (Formula I)

A mixture of pure L-(+)-tartrate salt of compound of formula Ib (19.0 g) and pure D-(−)-tartrate salt of compound of formula Ia (18.0 g) was suspended in 5% aqueous ethanol (370 mL), the suspended mixture was heated to reflux for 2 hours and gradually cooled to 25-30° C. in 3-4 hours. Reaction mass was stirred at 25-30° C. for 3 hours. The solid was filtered and washed with ethanol (16 mL) at 25-30° C. The solid was dried at 45-50° C. under vacuum to afford a pure compound (Weight: 29.0 g; Yield: 78.37%).

To a cooled (10-15° C.) solution of pure compound (27 g) in water (16.2 mL) was added 20% aqueous sodium hydroxide solution (27 mL) to adjust its pH to ~10 and stirred at 10-15° C. for 2 hours. The solid was filtered and washed with cold (10-15° C.) water. The solid was dried at 45-50° C. which was suspended in ethyl acetate (950 mL) and stirred under reflux for 2 hours. The undissolved solid was filtered off through micron. The filtrate was concentrated under vacuum to provide white solid mass which was dissolved in ethyl acetate (140 mL) under reflux, stirred for 2 hours. The solution was cooled to 25-30° C. and stirred for 16-18 hours. The precipitated solid was filtered and dried under vacuum at 40-45° C. to afford pure exametazime of formula I (Weight: 10.5 g; Yield: 46.87% (over 2 steps); Chiral Purity: d-isomer 49.41%, l-isomer 50.43%), meso-isomer ~0.16%.

Example 3

Preparation of Exametazime 'Formula I' Using dl Tartaric Acid: Method C
Step I: Preparation of Diimine Derivative 4,8-diaza-3,6,6,9-tetramethylundecane-3,8-diene-2,10-dione bisoxime (formula IV)

To a cooled (0-5° C.) solution of 2,3-butanedione monoxime (formula II; 118.6 g) and 2,2-dimethyl-1,3-propanediamine (formula II; 50.0 g) in acetonitrile (500 mL), was added calcium hydride (42.0 g) portionwise and solution was stirred at 0-5° C. for next 30 minutes and then allowed to warm to room temperature. The solution was slowly brought to reflux and kept under stirring at the same temperature for ~6-10 hours. The reaction mixture was cooled ~70° C., filtered through celite and washed with acetonitrile (200 mL). The filtrate was concentrated under vacuum to afford the title compound as an oily residue (Weight: 130.0 g; Yield: 99.23%).

Step II: Preparation of a Mixture of 'd', 'l' and Meso Isomers

To the cooled (0° C.) suspension of diimine derivative (formula IV; 130.0 g) in ethanol (750 mL), sodium borohydride (18.63 g) was added portionwise at 0-5° C. in 60 minutes and kept stirring at this temperature for 30 minutes. The reaction mass was concentrated under vacuum and then diluted with water (250 mL). The resulting suspended reaction mass was stirred at 5-10° C. for 16 hours and solid was filtered which was stirred under reflux in ethyl acetate (1800 mL) and filtered off the undissolved residue through celite. The filtrate was concentrated under vacuum at 40-45° C. to afford a white solid, which was recrystallized in acetonitrile at −10 to −20° C. to afford the title compound (Weight: 64.0 g; Yield: 48.74% (from step I); Chiral Purity: d-isomer ~24%, l-isomer ~24%, meso-isomer ~52%).

Step III: Preparation of Crude dl-Tartrate Salt of Exametazime (±)-Tartaric acid (11.0 g) was added to the suspended solution of 'd', 'l' and meso isomers (20.0 g), in isopropanol (600 mL). The resulting mixture was stirred under reflux for 2 hours, cooled to 25-30° C. in 2-3 hours and kept stirring at this temperature for 3 hours. The solid was filtered, washed with ethanol (20 mL) at 25-30° C. and dried at 40-45° C. under vacuum to afford the title compound (Weight: 17.2 g; Yield: 55.48%; Chiral Purity: d-isomer ~41.6%, l-isomer 40.5%, meso-isomer ~17.9%).

Step IV: Preparation of Pure dl-Tartrate Salt of Exametazime

The crude dl-tartrate salt of exametazime (17.0 g) was suspended in 5% aqueous ethanol (340 mL) heated to reflux for 2 hours and gradually cooled to 25-30° C. in 3-4 hours. Reaction mass was stirred at 25-30° C. for 3 hours. The solid was filtered and washed with 5% aqueous ethanol (10 mL) at 25-30° C. The solid was dried at 45-50° C. under vacuum to afford the title compound (Weight: 10.5 g; Yield: 61.76%; Chiral Purity: d-isomer ~47.22%, l-isomer 46.05%, meso isomer ~6.23%).

Step V: Preparation of Exametazime (Formula I)

To a cooled (10-15° C.) solution of pure dl-tartrate salt of exametazime (10.5 g) in water (6.2 mL), was added 20% aqueous sodium hydroxide solution (12 mL) to adjust its pH to ~10 and stirred for 2 hours at 10-15° C. The solid was filtered and washed with cold (10-15° C.) water (11.5 mL). The solid was dried at 45-50° C. which was suspended in ethyl acetate (350 mL) and stirred under reflux for 2 hours. The undissolved solid was filtered off through micron. The filtrate was concentrated under vacuum to provide white solid mass which was dissolved in ethyl acetate (50 mL) under reflux, stirred for 2 hours. The solution was cooled to 25-30° C. and stirred for 16-18 hours. The precipitated solid was filtered and dried under vacuum at 40-45° C. to afford exametazime of formula I (Weight: 5.0 g; Yield: 73.43%; Chiral Purity: d-isomer 49.57%, l-isomer 50.03%, meso-isomer 0.41%).

We claim:
1. A process for the preparation of exametazime (formula I),

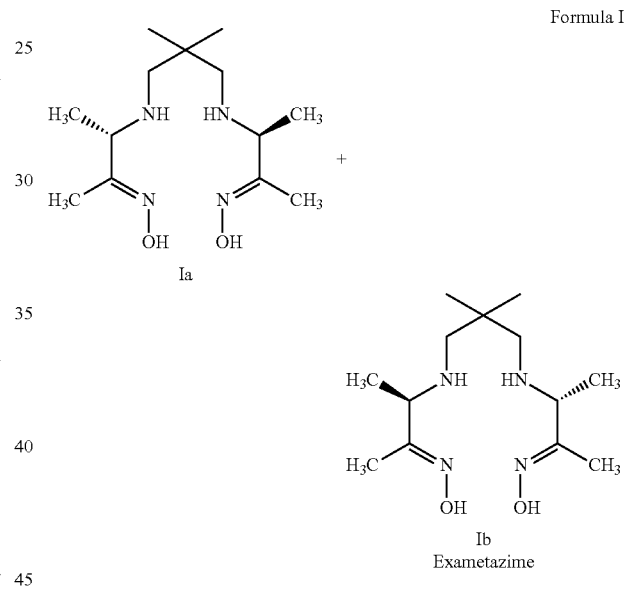

which comprises the steps of:
a) reacting 2,3-butanedione monoxime (formula II) with 2,2-dimethyl-1,3-propanediamine (formula III), in a suitable solvent, in presence of a dehydrating agent to afford diimine derivative 4,8-diaza-3,6,6,9-tetramethylundecane-3,8-diene-2,10-dione bisoxime (formula IV),

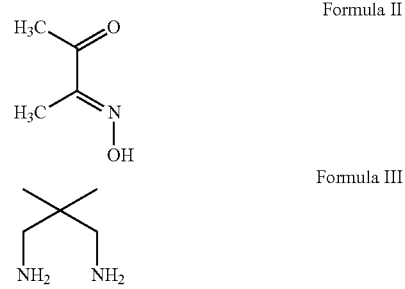

-continued

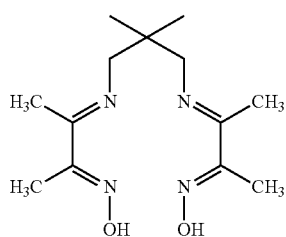

Formula IV b) reducing diimine derivative 4,8-diaza-3,6,6,9-tetramethylundecane-3,8-diene-2,10-dione bisoxime (formula IV) with a suitable reducing agent in a suitable solvent to afford a mixture of 'd', 'l' and meso isomers,

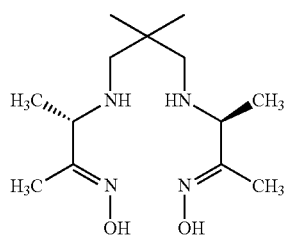

Ia

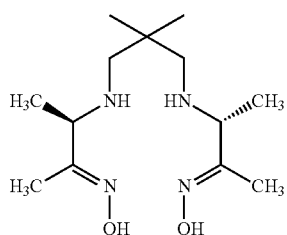

Ib

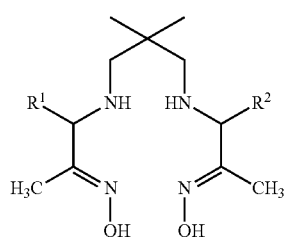

Ic

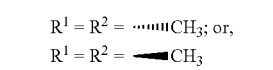

c) optionally, purifying the mixture of 'd', 'l' and meso isomers,
d) treating the mixture of 'd', 'l' and meso isomers with d or l chiral resolving acid to form corresponding acid addition salts, which are enantiomers of exametazime, and separating one of the enantiomers of exametazime as an acid addition salt,
e) optionally, purifying the acid addition salt obtained in step (d),
f) treating the mother liquor of step (d) with a suitable base,
g) isolating a mixture of 'd' or 'l' enantiomers and meso isomers,
h) purifying the mixture obtained in step (g),
i) treating the mixture from step (h) with l or d chiral resolving acid to form corresponding acid addition salts, which are other enantiomers of exametazime and separating said other enantiomers of exametazime as acid addition salts,
j) optionally, purifying the acid addition salts obtained in step (i),
k) mixing the acid addition salt of step (d) or (e) and step (i) or (j),
l) optionally, purifying the mixture of acid addition salts obtained in step (k),
m) treating the mixture of acid addition salts of step (k) or (l) with a suitable base to afford exametazime and,
n) optionally, purifying the exametazime.

2. The process according to claim 1, wherein the dehydrating agents is selected from the group consisting of calcium hydride, molecular sieves, magnesium sulphate and sodium sulphate.

3. The process according to claim 1, wherein the chiral resolving acid is selected from the group consisting of L-(+) tartaric acid, D-(−) tartaric acid, L-malic acid, D-malic acid, S-(+) mandelic acid, R-(−) mandelic acid, S-(+)-O-acetyl mandelic acid, R-(−)-O-acetyl mandelic acid, (−)-naproxen, (+)-naproxen, (1R)-(−)-camphor sulfonic acid, (1S)-(+)-camphor sulfonic acid, (1R)-(+)-bromocamphor-10-sulfonic acid, (1S)-(−)-bromocamphor-10-sulfonic acid, (−)-Dibenzoyl-L-tartaric acid, (−)-Dibenzoyl-L-tartaric acid monohydrate, (+)-Dibenzoyl-D-tartaric acid, (+)-Dibenzoyl-D-tartaric acid monohydrate, (+)-dipara-tolyl-D-tataric acid, (−)-dipara-tolyl-L-tataricacid, L(−)-pyroglutamic acid, L(+)-pyroglutamic acid, (+)-lactic acid, (−)-lactic acid, (S)-(+)-2-chloromandelic acid, and (R)-(−)-2-chloromandelic acid.

4. The process according to claim 1, wherein the 'd' and 'l' mixture of chiral resolving acid is selected from the group consisting of (±) tartaric acid, (±) malic acid, (±) ascorbic acid, (±) mandelic acid, (±)-O-acetyl mandelic acid, (±) naproxen, (±) camphor sulfonic acid, (±) bromocamphor-10-sulfonic acid, (±) Dibenzoyl-tartaric acid, (±) dipara-tolyl-tataric acid, (±) pyroglutamic acid, (±) lactic acid, and (±)-2-chloromandelic acid.

5. The process according to claim 1, wherein the suitable bases is selected from the group consisting of sodium hydroxide, potassium hydroxide, sodium carbonate, potassium carbonate, sodium bicarbonate, and potassium bicarbonate, either alone or as their aqueous solutions.

6. The process according to claim 1, wherein the suitable solvents is selected from the group consisting of nitriles, alcohols, esters, halogenated hydrocarbons, ethers, amides, dialkylsulfoxides, hydrocarbons, water and a mixture thereof; with the proviso that ketones/nitriles are not used during the reduction reaction of diimine derivative 4,8-diaza-3,6,6,9-tetramethylundecane-3,8-diene-2,10-dione bisoxime (formula IV); and water is avoided in condensation of 2,3-butanedione monoxime (formula II) with 2,2-dimethyl-1,3-propanediamine (formula III).

* * * * *